(12) United States Patent
Borden

(10) Patent No.: US 11,284,874 B2
(45) Date of Patent: Mar. 29, 2022

(54) SNAP LOCK

(71) Applicant: Peter Scott Borden, Torrance, CA (US)

(72) Inventor: Peter Scott Borden, Torrance, CA (US)

( * ) Notice: Subject to any disclaimer, the term of this patent is extended or adjusted under 35 U.S.C. 154(b) by 172 days.

(21) Appl. No.: 15/729,054

(22) Filed: Oct. 10, 2017

(65) Prior Publication Data

US 2018/0098762 A1 Apr. 12, 2018

Related U.S. Application Data

(60) Provisional application No. 62/406,656, filed on Oct. 11, 2016.

(51) Int. Cl.
*A61B 17/04* (2006.01)
*A61B 17/06* (2006.01)

(52) U.S. Cl.
CPC .... *A61B 17/0401* (2013.01); *A61B 17/06166* (2013.01); *A61B 2017/0409* (2013.01); *A61B 2017/0414* (2013.01); *A61B 2017/0496* (2013.01)

(58) Field of Classification Search
CPC .............. A61B 17/0487; A61B 17/686; A61B 17/0401; A61B 2017/0409; A61B 2017/0414; A61B 2017/0458; A61B 2017/0412; A61B 2017/0445; A61B 2017/0464; A61B 2017/0496; A61B 2017/0454; A61B 2017/0432; A61B 2017/0433; A61B 2017/0424; A61B 2017/0425; A61B 2017/0438; A61F 2002/087; A61F 2002/0858; A61F 2002/0864

See application file for complete search history.

(56) References Cited

U.S. PATENT DOCUMENTS

| | | | | |
|---|---|---|---|---|
| 7,517,357 B2 * | 4/2009 | Abrams | ............. | A61B 17/0401 606/232 |
| 9,144,425 B2 | 9/2015 | Kaplan | | |
| 2006/0235410 A1 * | 10/2006 | Ralph | .................. | A61B 17/686 606/313 |
| 2009/0292321 A1 * | 11/2009 | Collette | ................ | A61F 2/0811 606/303 |
| 2010/0262185 A1 | 10/2010 | Gelfand et al. | | |

(Continued)

*Primary Examiner* — Wade Miles
*Assistant Examiner* — Mikail A Mannan
(74) *Attorney, Agent, or Firm* — Jeffrey F. Yee; Lewis, Brisbois, Bisgaard & Smith LLP

(57) ABSTRACT

A lock and method for suspending suture(s) from bone and providing a secure fixation of the suture(s) within the lock including a generally cylindrical outer shell having a tapered interior cavity or canal and tapered inner wall and a distal end, a generally cylindrical plug having a tapered exterior peripheral surface sized and adapted to be insertable into the outer shell cavity and to form a tight, compression holding or fixation of the suture to the lock, and the plug having a radially extending shoulder or protrusion, whereby insertion of the inner plug into the shell causes, the shoulder or protrusion to expand or snap outwardly and over the distal end of the outer shell and to lock the plug to the outer shell, whereby the suture(s) are locked into place within and to the shell, thereby providing rigid fixation and compression of the suture material.

5 Claims, 7 Drawing Sheets

(56) References Cited

U.S. PATENT DOCUMENTS

2011/0046682 A1* 2/2011 Stephan ............... A61B 17/686
                                                      606/305
2014/0194907 A1* 7/2014 Bonutti ................ A61F 2/0811
                                                      606/151
2017/0209139 A1    7/2017 Burkhart et al.

* cited by examiner

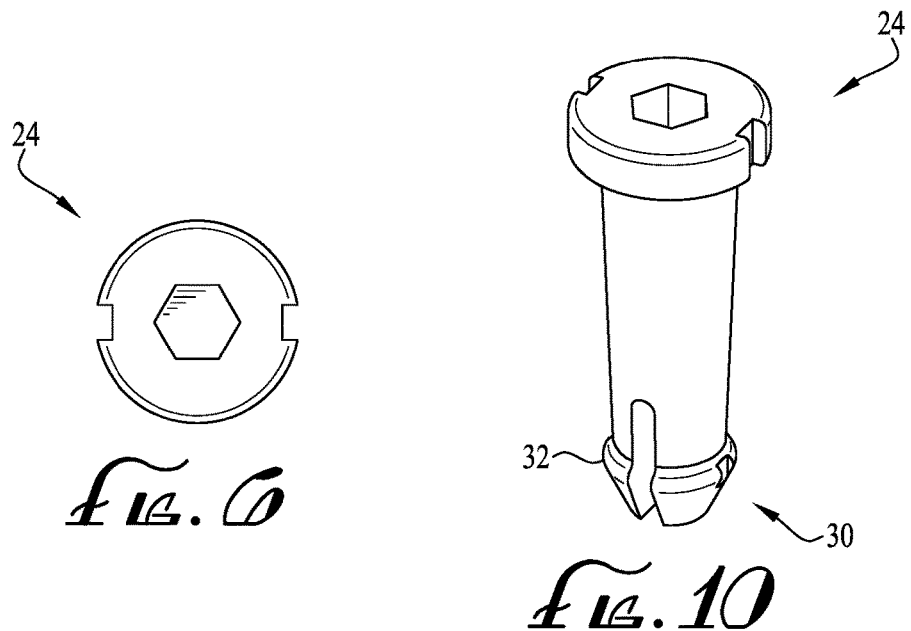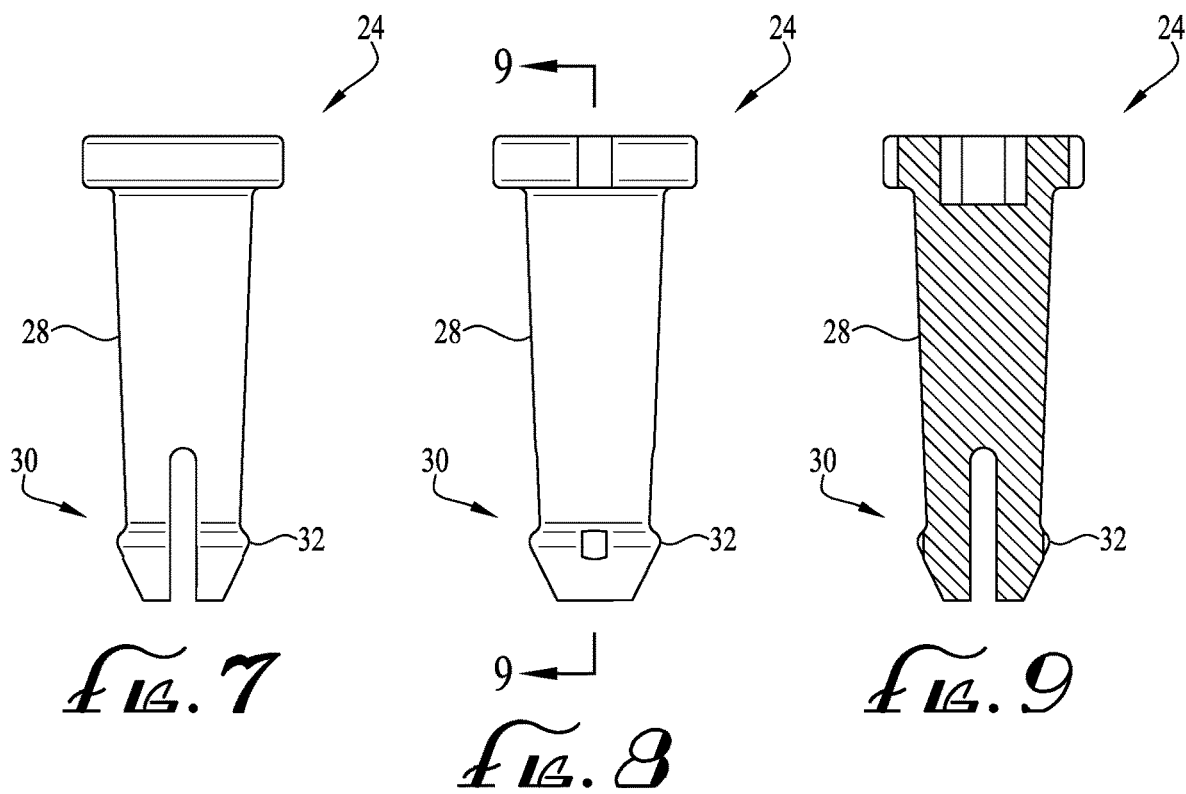

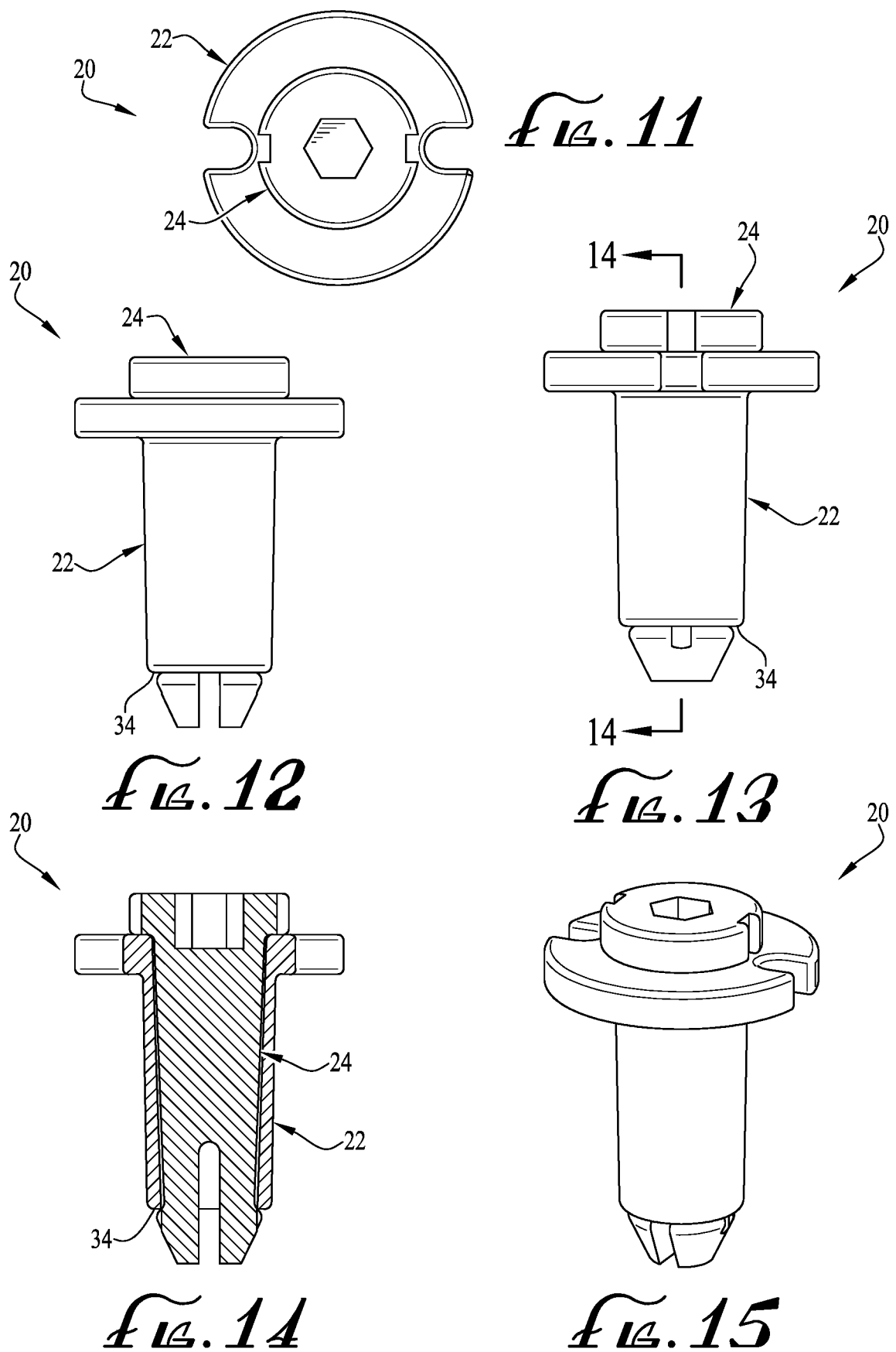

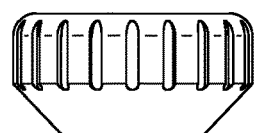
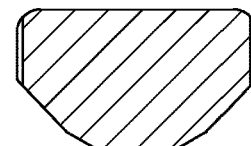
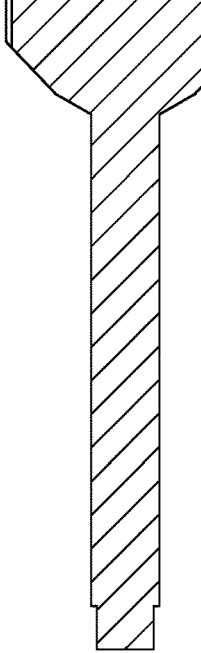
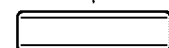
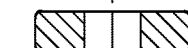
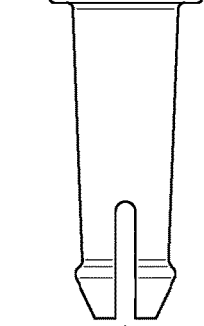
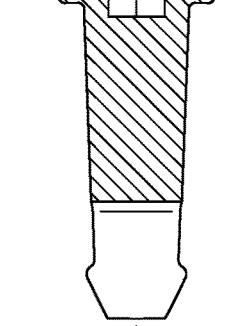
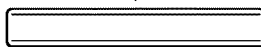
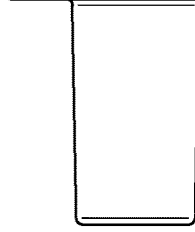
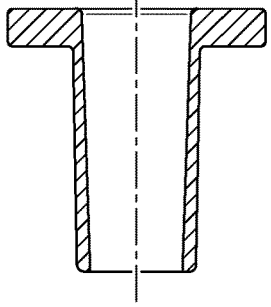
fig.23  fig.24

SNAP LOCK

FIELD OF INVENTION

The invention relates generally to the field of surgery and is intended to allow for improved fixation of soft tissue to bone.

BACKGROUND

Devices and methods of suspending suture(s) from bone are known. However, these devices and methods typically require knotting the suture(s), and expose the suspended suture(s) to loosening and/or untying.

SUMMARY

The snap lock and method of implementation according to the present invention overcome the drawbacks of known suture lock devices and methods of implementation by providing multiple points of fixation of the suture and without knotting the suture.

This invention relates to an apparatus and method for suspending suture from bone and providing a secure fixation of the suture within the device. The specific design of the device allows for tensioning of various sized suture material or suture tape that has been passed through the device. After the sutures are pulled through the apparatus member to the desired position of fixation, a second internal member of the apparatus is advanced and snapped into the apparatus which provides for multiple points of fixation against the suture. The unique internal compression mechanism allows for three different points of compression against the suture material which allows for superior fixation. Embodiments of the presently described snap lock accomplish knotless fixation of soft tissue to bone.

The present snap lock is intended to be used in the reconstruction of soft tissue disruption such as ligament or tendon tears. This lock and its implementation avoid the need for suture tying and are intended for use in various areas of the musculoskeletal system. By providing secure fixation of the tissue within the bone, the body part may be rehabilitated more aggressively and thereby reducing post-operative complications such as stiffness of a joint and improve recovery time following surgery.

Implementation of the present snap lock includes drilling or reaming a desired size hole into bone. Sutures are then passed through the hole and then passed through the lock. The lock is then inserted into the hole and pressed against the bone. The sutures are then pulled through the lock to the desired tension. The tissue intended for fixation has already been attached to the opposite end of the sutures. Once satisfactory positioning of the tissue is achieved, the snap lock is operated or tightened by advancing the internal piece which snaps into place when fully seated into the outer piece. This locks and compresses the sutures against the inner wall of the outer piece. This allows for completion of the ligament fixation.

The present invention allows for fastening of suture through a predrilled hole by compression of the suture between pieces of the apparatus. Prior to passing the suture through the device, it is attached to tissue (such as ligament, tendon, or bone) that is intended to be "fixed".

These and other embodiments, features, aspects, and advantages of the invention will become better understood with regard to the following description, appended claims and accompanying drawings.

BRIEF DESCRIPTION OF THE DRAWINGS

The foregoing aspects and the attendant advantages of the present invention will become more readily appreciated by reference to the following detailed description, when taken in conjunction with the accompanying drawings, wherein:

FIG. 6 is a perspective top view of the snap lock inner piece;

FIG. 7 is a perspective side view of the snap lock inner piece demonstrating the distal slot intended for narrowing of the piece as it is advanced into the outer piece; and the outward protruding shoulder allowing for the "locking" mechanism after the inner piece is fully seated into the outer piece;

FIG. 8 is a perspective side view of the snap lock inner piece on the side that is not slotted distally;

FIG. 9 is a perspective cross section side view of the inner piece;

FIG. 10 is a perspective top side view of the snap lock inner piece;

FIG. 11 is a perspective top view of the snap lock inner and outer pieces after being snapped into place;

FIG. 12 is a perspective side view of the snap lock inner and outer pieces after being snapped into place and demonstrating the view of the slot of the inner piece;

FIG. 13 is a perspective side view of the snap lock inner and outer pieces after being snapped into place and demonstrating the non-slotted inner piece;

FIG. 14 is a perspective cross sectional side view of the snap lock inner and outer pieces after being snapped into place;

FIG. 15 is a perspective top side view of the snap lock inner and outer pieces after being snapped into place;

FIG. 23 is an exploded, perspective view of a preferred embodiment of an insertion instrument or tool for use with the FIGS. 1-22 embodiment; and, FIG. 24 is a side, cross-sectional view of the FIG. 23 insertion tool embodiment.

DETAILED DESCRIPTION

Figure 1:
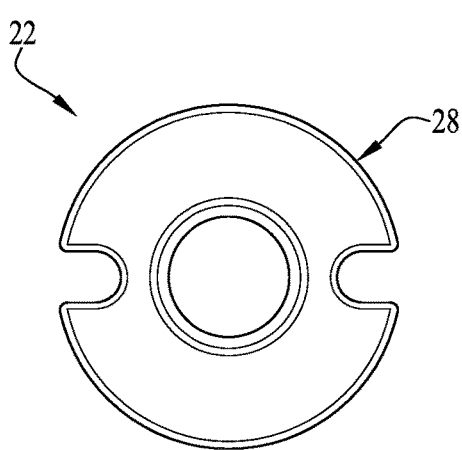
FIG. 1 is a perspective top view of a preferred embodiment snap lock outer piece.
Figure 2:
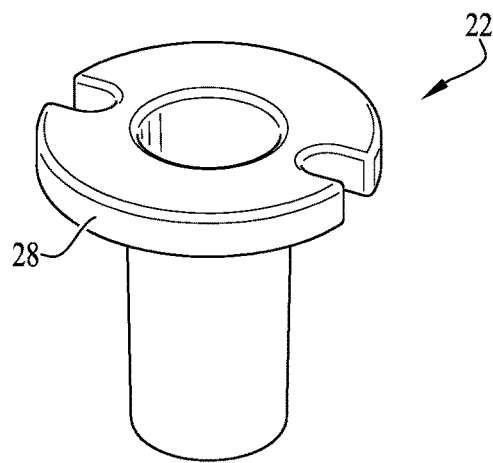
FIG. 2 is a perspective top side view of the snap lock outer piece.
Figure 3:
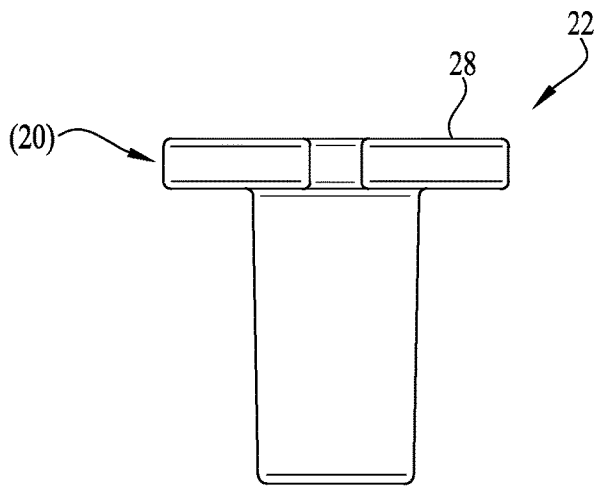
FIG. 3 is a perspective side view of the snap lock outer piece with a view of the anti-rotational slot.
Figure 4:
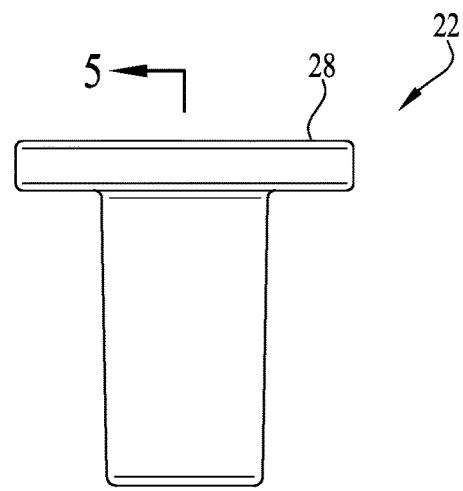
FIG. 4 is a perspective side view of the snap lock outer piece of the side without the anti-rotational slot.
Figure 5:
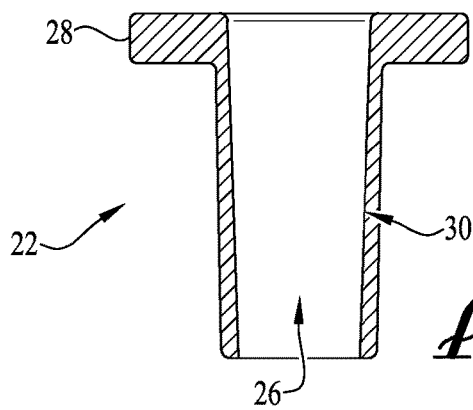
FIG. 5 is a perspective cross section side view of the snap lock outer piece of the inside of the outer piece demonstrating the tapered inner portion.
Figure 16:
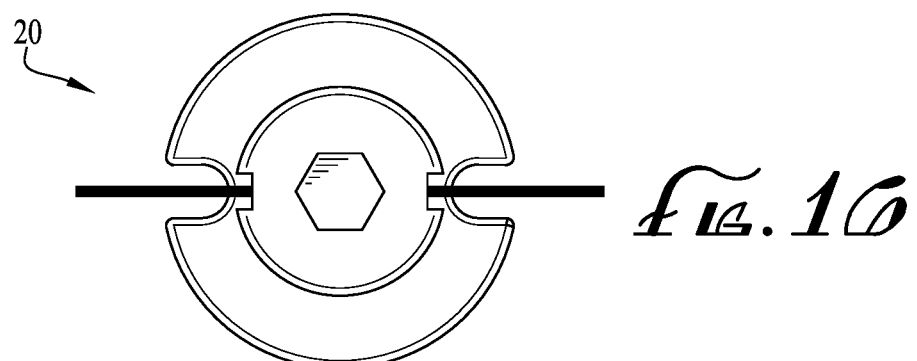
FIG. 16 is a perspective top view of the snap lock after passage of suture material and after the inner and outer pieces are snapped into place.
Figure 17:
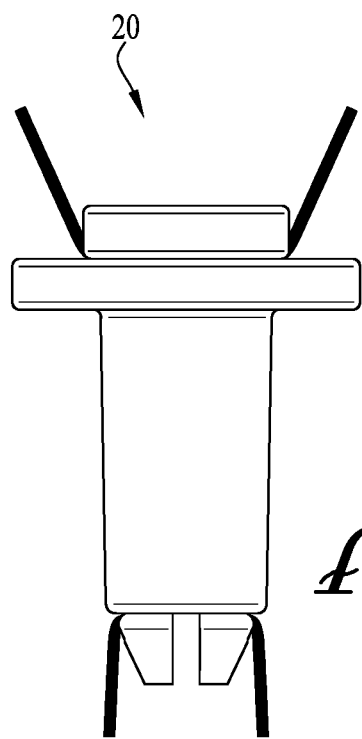
FIG. 17 is a perspective side view of the snap lock after passage of suture material and after the inner and outer pieces are snapped into place demonstrating the slotted side of the inner piece.
Figure 18:
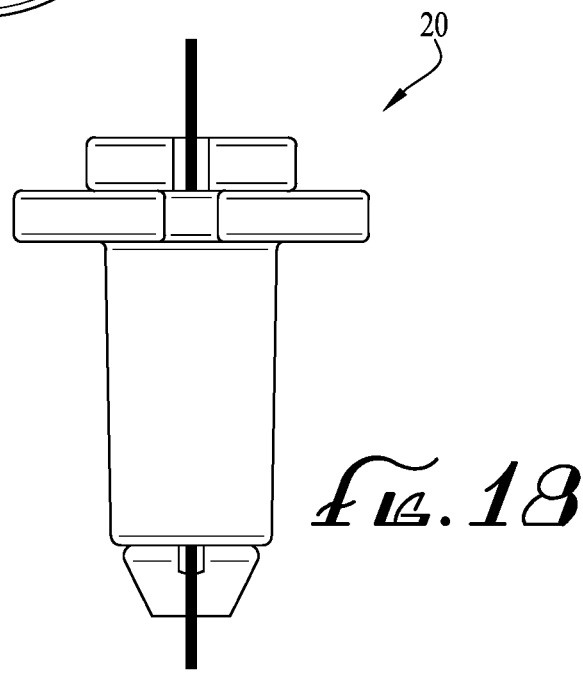
FIG. 18 is a perspective side view of the snap lock after passage of suture material and after the inner and outer pieces are snapped into place demonstrating the non-slotted side of the inner piece.
Figure 19:
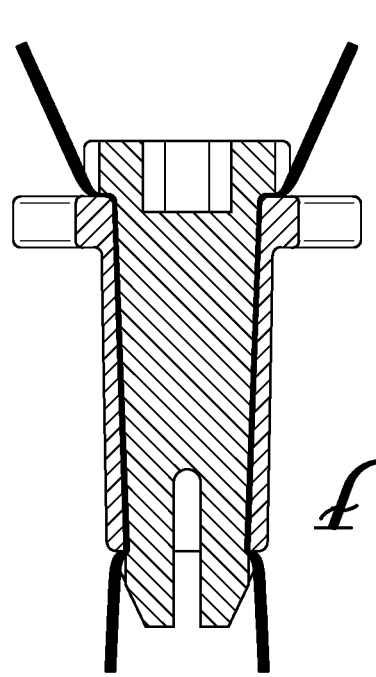
FIG. 19 is a perspective cross sectional side view of the snap lock after passage of suture material and after the inner and outer pieces are snapped into place.
Figure 20:
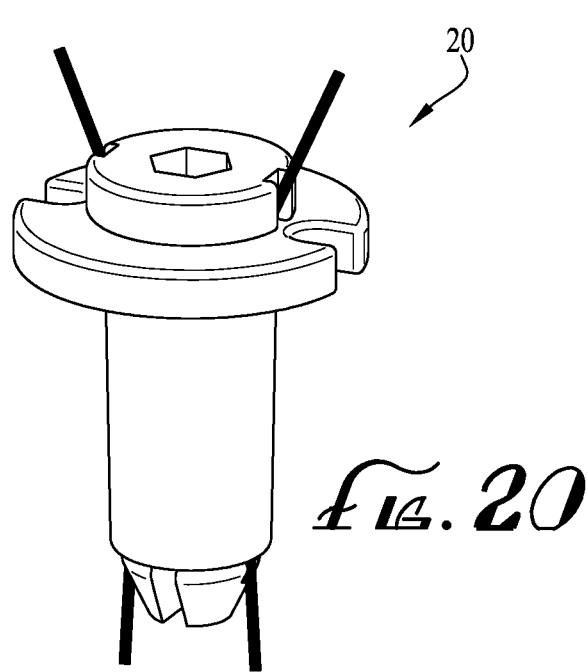
FIG. 20 is a top side view of the snap lock after passage of suture material and after the inner and outer pieces are snapped into place.
Figure 21:
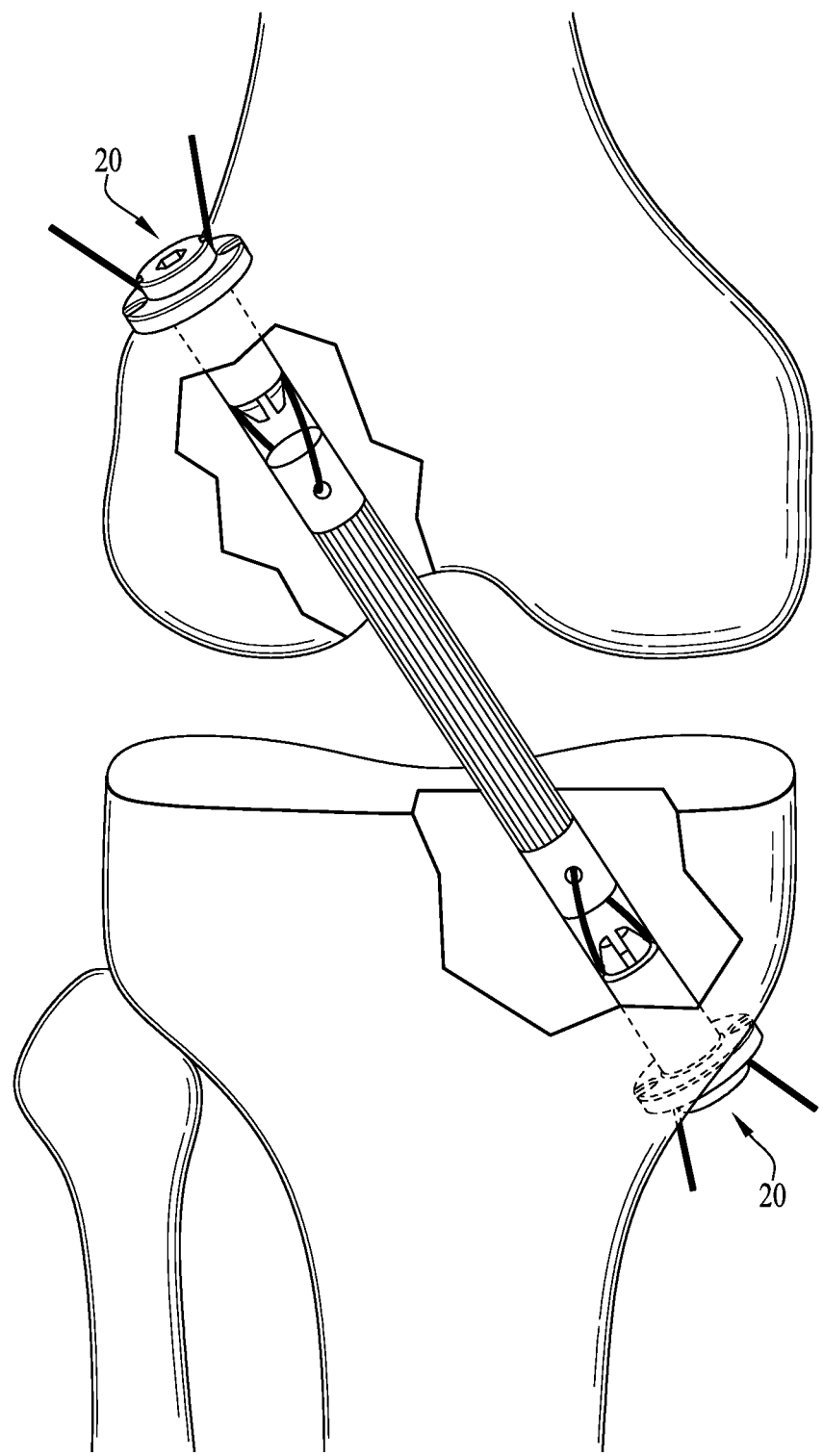
FIG. 21 is a drawing demonstrating application of the snap lock fixation device for fixation of anterior cruciate ligament reconstruction.
Figure 22:
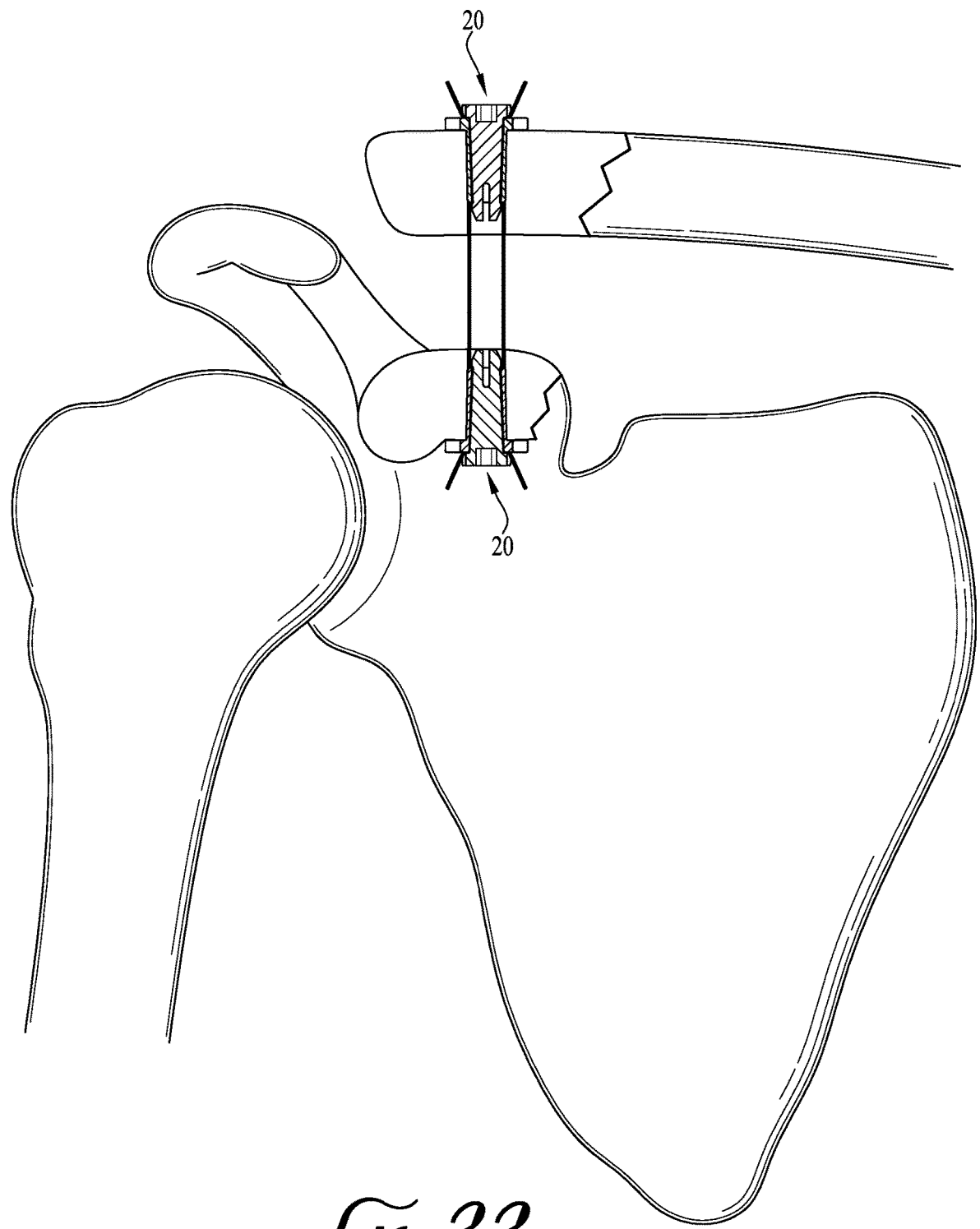
FIG. 22 is a drawing demonstrating application of the snap lock fixation device for fixation of an acromial clavicular joint dislocation.

In accordance with embodiments described herein, embodiments of the presently described snap lock 20, illustrated in FIGS. 11-15, includes an outer piece hollow, shell 22 as illustrated in FIGS. 1-5, and an inner piece 24 as illustrated in FIGS. 6-10. The shell 22 is also referred to as a body, is generally of a hollow, cylindrical configuration, preferably with its inner diameter tapered or narrowed from the top down to the bottom. During a surgical procedure, as illustrated in FIGS. 21-22, the shell 22 is inserted into a pre-drilled hole within bone. The shell 22 includes a hollowed, tapered shaft, or canal 26, having a predetermined inner diameter and extending downward from a wider diameter collar or top flange 28. The shell 22 is preferably of a one-piece construction, as shown in FIG. 5. The outer of the shell, i.e., the surfaces at the outer diameter, may be smooth, roughened or screw shaped with a threaded, tapered pitch.

Canal 26 is adapted and sized to snuggly receive a tapered shaft 28 part of the inner piece or component 24 as shown by arrow 30 in FIG. 5.

During a surgical procedure, the inner piece 24 is advanced or inserted into canal 26 of the outer piece 22, preferably by an inserter instrument as illustrated in FIGS. 23-24. As shown in FIGS. 7, 9 and 10, the distal end of the inner piece 24 includes, preferably, a slotted tip 30, which functions to permit squeezing and narrowing of the diameter of the distal end during insertion. As the distal end of inner piece 24 is advanced toward and beyond the distal end of the outer piece 22, the tip 30 of the inner piece narrows to allow passage and then returns, or snaps back to its original position outside of the distal end of the outer piece. This snapping action locks the two components together, as shown in FIGS. 11-15. Referring to FIGS. 7-10, the inner piece distal end, at tip 30 has a rigid slight prominence or radially outwardly protruding shoulder 32 that hooks or snaps outwardly onto the tip 34 of outer piece 22, as shown in FIGS. 12-15. Once fully advanced and snapped into place, the shoulder 32 prevents the inner piece 24 from retracting backwards and separating from the outer piece 22. The outer and inner pieces 22, 24 respectively, may be made of various types of materials that have the ability to provide a secure fastening and to provide the snapping functionality as described herein. For example, the materials of construction can include PEEK, composite, or metal. The outer and inner pieces may also have a smooth or roughened surface or of a smooth or rough-surfaced material.

The clinical application of embodiments of the invention involves passing sutures through the tip of the distal end of the outer piece (shell) and up through the central canal of the outer piece (shell) and out the top of the outer piece (shell). The inner piece or tapered, cylindrical plug is then advanced into the outer piece until fully seated and locks into place as the tip of the inner piece returns or snaps and locks into its original position, with the projection of the tip of the inner piece extending radially outward or beyond outer diameter of the outer piece. This snap locking function compresses the sutures at the distal end tip of the outer piece (shell) and also against the inner walls of the outer piece. Finally, when the inner piece is advanced completely, it's head or top flange or collar 28 engages and presses the sutures against the outer rim of the top, or proximal end of the outer piece (shell) to provide a third area of compression/fixation as shown in FIGS. 16-20. This multiple-point compression of the suture material between the two pieces or components of the snap lock provides optimal knotless fixation.

The presently preferred internal snap-in mechanism shown and described herein provides for multiple points of fixation of variously sized (thickness and width) suture material. This allows for optimal positioning of the ligament reconstruction. For example, if the fixture device is used on both sides of the knee for an ACL reconstruction, the tissue graft can be advanced into the femur or tibia and adjusted from either end of the graft, as shown in Figure. This exemplary way of fixation may avoid a significant problem known to be associated with bone tendon bone reconstructions, and commonly referred to as "tunnel mismatch." The presently described fixation lock and method of implementation also permits performing these types of reconstructions without the need for fixation of the tissue within the socket (such as with interference screws). The collar portion 28 of the body or shell also can function to plug the hole preventing leakage of important fluids involved in the ligament healing process. The presently described snap lock also functions to permit fixation of tissue through small incisions which in turn avoids further soft tissue damage associated with more invasive exposures. Another exemplary application is for use in the shoulder for reconstruction of the ligaments following an acromial clavicular dislocation, as shown in FIG. 22.

The present snap lock may be developed with slight variations of the internal or outer components for the same multiple point fixation.

The present snap lock may be used in various areas of the body such as the knee, shoulder, ankle, and hip for stabilization of joints with ligament laxity.

Although specific embodiments of the invention have been described, various modifications, alterations, alternative constructions, and equivalents are also encompassed within the scope of the invention.

The specification and drawings are, accordingly, to be regarded in an illustrative rather than a restrictive sense. It will, however, be evident that additions, subtractions, deletions, and other modifications and changes may be made thereunto without departing from the broader spirit and scope of the invention as set forth in the claims.

What is claimed is:

1. A suture snap lock comprising:
    a shell having a generally cylindrical outer shell body, having an interior cylindrical tapered cavity extending along a tapered wall having a smooth inner surface of a predetermined length that extends along the entire length of the outer shell body, an open bottom end wherein the open bottom end having an outer diameter, the outer shell body having an open top end and a top end flange extending radially outward from said top end;
    an inner cylindrical piece that is adapted to be inserted into the interior cylindrical tapered cavity of the shell body and locked into the outer shell body when fully inserted, wherein the inner surface of the interior cylindrical tapered cavity of the shell body is sized to substantially match the geometry contour of the outer surface of the inner cylindrical piece such that the inner cylindrical piece is snuggly received into the interior cylindrical tapered cavity of the shell body;

the inner cylindrical piece having a top proximal end, a bottom distal end, and a slotted tip at the tip of the bottom distal end that permits squeezing and narrowing of the diameter of the bottom distal end during insertion;

the inner cylindrical piece's bottom distal end including a radially outwardly projecting shoulder having an outer diameter greater than the shell body open bottom end's inner diameter;

whereby suture positioned between the inner cylindrical piece and the outer cylindrical shell body is compressed and retained between the inner cylindrical piece and the outer cylindrical shell body when said inner cylindrical piece is fully advanced into the outer shell body and locks said cylindrical piece into said outer shell body.

2. The snap lock of claim 1, wherein the outer shell body and the inner cylindrical piece are made of a metal.

3. The snap lock of claim 1, wherein the outer shell body and the inner cylindrical piece are made of PEEK.

4. The snap lock of claim 1, wherein the outer shell body and the inner cylindrical piece are made of a composite material.

5. A snap lock comprising:

a shell having a generally cylindrical outer shell body, having an interior cylindrical tapered cavity extending along a smooth surfaced, tapered wall extending along a predetermined length of the entire length of the outer shell body, an open bottom end, an open top, end and a top end flange extending radially outward from said top end;

an inner cylindrical piece having a top proximal end, a bottom distal end and a slotted tip at the tip of the bottom distal end that permits squeezing and narrowing of the diameter of the bottom distal end during insertion; the inner surface of the interior cylindrical tapered cavity of the shell body is sized to substantially match the geometry contour of the outer surface of the inner cylindrical piece such that the inner cylindrical piece is snuggly received into the interior cylindrical tapered cavity of the shell body;

the inner cylindrical piece's bottom distal end including a radially outwardly projecting shoulder, the shoulder having an outer periphery extending radially outward from the inner cylindrical piece's outer surface near the bottom distal end;

suture material positioned between the inner cylindrical piece and the outer cylindrical shell body;

whereby said suture material is compressed and retained between the inner cylindrical piece and outer shell body, and the cylindrical piece is locked into said outer shell body when the inner cylindrical piece is inserted into the shell body cavity.

\* \* \* \* \*